(12) United States Patent
McCullough, Jr. et al.

(10) Patent No.: US 9,655,673 B2
(45) Date of Patent: May 23, 2017

(54) SURGICAL INSTRUMENT

(71) Applicant: COVIDIEN LP, Mansfield, MA (US)

(72) Inventors: Robert F. McCullough, Jr., Boulder, CO (US); Ryan C. Artale, Boulder, CO (US); Robert M. Sharp, Boulder, CO (US); Tony Moua, Broomfield, CO (US); Mark J. Huseman, Broomfield, CO (US); Audrey Earnshaw, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 149 days.

(21) Appl. No.: 14/196,066

(22) Filed: Mar. 4, 2014

(65) Prior Publication Data

US 2014/0257274 A1 Sep. 11, 2014

Related U.S. Application Data

(60) Provisional application No. 61/776,136, filed on Mar. 11, 2013.

(51) Int. Cl.
| | | |
|---|---|---|
| *A61B 18/18* | (2006.01) | |
| *A61B 18/14* | (2006.01) | |
| *A61B 17/29* | (2006.01) | |
| *A61B 18/00* | (2006.01) | |
| *A61B 90/00* | (2016.01) | |

(52) U.S. Cl.
CPC .... *A61B 18/1445* (2013.01); *A61B 2017/292* (2013.01); *A61B 2018/0063* (2013.01);
(Continued)

(58) Field of Classification Search
CPC ........ A61B 18/1445; A61B 2018/0063; A61B 18/1447; A61B 18/1482; A61B 2017/292;
(Continued)

(56) References Cited

U.S. PATENT DOCUMENTS

| | | |
|---|---|---|
| 3,100,489 A | 8/1963 | Bagley |
| D249,549 S | 9/1978 | Pike |
| | (Continued) | |

FOREIGN PATENT DOCUMENTS

| | | |
|---|---|---|
| CN | 201299462 | 9/2009 |
| DE | 2415263 A1 | 10/1975 |
| | (Continued) | |

OTHER PUBLICATIONS

Extended European Search Report from Application No. 14158819.4 dated Jun. 10, 2014.
(Continued)

*Primary Examiner* — Michael Peffley
*Assistant Examiner* — Amanda Zink

(57) ABSTRACT

An electrosurgical instrument includes a housing including an elongated shaft. A stationary actuation member is axially disposed within the elongated shaft and includes a cam pin. An actuating mechanism is operably coupled to the elongated shaft and is moveable relative to the housing to selectively cause movement of the elongated shaft. An end effector includes a pair of opposing first and second jaw members operably coupled about a common pivot. One or both of the jaw members includes a camming slot configured to engage the cam pin. Each jaw member includes an electrically conductive tissue sealing surface adapted to connect to a source of electrosurgical energy. A knife blade is supported in the elongated shaft and moveable in a longitudinal direction to cut tissue disposed between the jaw members. A switch is configured to be engaged by the actuating mechanism to initiate delivery of electrosurgical energy to tissue.

20 Claims, 14 Drawing Sheets

(52) U.S. Cl.
CPC .......... *A61B 2018/00601* (2013.01); *A61B 2018/00928* (2013.01); *A61B 2018/1455* (2013.01); *A61B 2090/031* (2016.02)

(58) Field of Classification Search
CPC  A61B 2018/00601; A61B 2018/00928; A61B 2018/1455; A61B 2019/301
USPC .................................................. 606/45–52
See application file for complete search history.

(56) References Cited

U.S. PATENT DOCUMENTS

| | | |
|---|---|---|
| D263,020 S | 2/1982 | Rau, III |
| 4,461,297 A | 7/1984 | Sutter |
| 4,461,305 A | 7/1984 | Cibley |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,122,139 A | 6/1992 | Sutter |
| 5,211,655 A | 5/1993 | Hasson |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,383,875 A | 1/1995 | Bays et al. |
| D358,887 S | 5/1995 | Feinberg |
| 5,454,827 A | 10/1995 | Aust et al. |
| 5,478,351 A | 12/1995 | Meade et al. |
| 5,512,721 A | 4/1996 | Young et al. |
| 5,601,601 A | 2/1997 | Tal et al. |
| D384,413 S | 9/1997 | Zlock et al. |
| 5,746,739 A | 5/1998 | Sutter |
| H1745 H | 8/1998 | Paraschac |
| D402,028 S | 12/1998 | Grimm et al. |
| 5,849,022 A * | 12/1998 | Sakashita .............. A61B 17/29 606/174 |
| D408,018 S | 4/1999 | McNaughton |
| 5,891,140 A | 4/1999 | Ginn et al. |
| 5,891,142 A | 4/1999 | Eggers et al. |
| D416,089 S | 11/1999 | Barton et al. |
| 6,010,516 A | 1/2000 | Hulka |
| D424,694 S | 5/2000 | Tetzlaff et al. |
| D425,201 S | 5/2000 | Tetzlaff et al. |
| 6,106,542 A | 8/2000 | Toybin et al. |
| 6,117,158 A | 9/2000 | Measamer et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,613 B2 | 8/2006 | Treat |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,166,106 B2 | 1/2007 | Bartel et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| 7,211,079 B2 | 5/2007 | Treat |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,791 B2 | 12/2009 | Garrison et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,922,718 B2 | 4/2011 | Moses et al. |
| D649,249 S | 11/2011 | Guerra |
| D649,643 S | 11/2011 | Allen, IV et al. |
| 8,152,806 B2 | 4/2012 | Black et al. |
| D661,394 S | 6/2012 | Romero et al. |
| 2002/0188294 A1 | 12/2002 | Couture et al. |
| 2003/0018331 A1 * | 1/2003 | Dycus ................ A61B 18/1445 606/48 |
| 2003/0109875 A1 | 6/2003 | Tetzlaff et al. |
| 2003/0171747 A1 | 9/2003 | Kanehira et al. |
| 2003/0229344 A1 * | 12/2003 | Dycus ................ A61B 18/1445 606/51 |
| 2004/0176762 A1 | 9/2004 | Lawes et al. |
| 2004/0243125 A1 * | 12/2004 | Dycus ................ A61B 18/1445 606/51 |
| 2005/0154387 A1 | 7/2005 | Moses et al. |
| 2007/0260241 A1 | 11/2007 | Dalla Betta et al. |
| 2008/0114349 A1 | 5/2008 | Treat |
| 2008/0215048 A1 | 9/2008 | Hafner et al. |
| 2008/0262491 A1 | 10/2008 | Swoyer et al. |
| 2010/0030205 A1 | 2/2010 | Herzon |
| 2010/0179540 A1 | 7/2010 | Marczyk et al. |
| 2011/0184459 A1 | 7/2011 | Malkowski et al. |
| 2011/0190765 A1 | 8/2011 | Chojin |
| 2011/0251613 A1 | 10/2011 | Guerra et al. |
| 2011/0301592 A1 | 12/2011 | Kerr et al. |
| 2012/0022524 A1 | 1/2012 | Timm et al. |
| 2012/0022529 A1 | 1/2012 | Shelton, IV et al. |
| 2012/0136347 A1 | 5/2012 | Brustad et al. |
| 2013/0018411 A1 | 1/2013 | Collings et al. |
| 2014/0257284 A1 * | 9/2014 | Artale ................ A61B 18/1445 606/49 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1645238 A1 | 4/2006 |

(56) References Cited

FOREIGN PATENT DOCUMENTS

| | | |
|---|---|---|
| EP | 1810625 A1 | 7/2007 |
| EP | 2347725 A1 | 7/2011 |
| EP | 2436330 A1 | 4/2012 |
| EP | 2659848 A2 | 11/2013 |
| EP | 2659849 A2 | 11/2013 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 02/080799 A1 | 10/2002 |
| WO | 2006/021269 A1 | 3/2006 |
| WO | 2005110264 A3 | 4/2006 |
| WO | 2008/040483 A1 | 4/2008 |
| WO | 2008/045348 A2 | 4/2008 |
| WO | 2011/018154 A1 | 2/2011 |
| WO | 2011/044343 A2 | 4/2011 |

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal hysterectomy" Obstetrics & Gynecology, vol. 102, No. 1, Jul. 2003.

"Reducing Needlestick Injuries in the Operating Room" Sales/Product Literature 2001.

(56) References Cited

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Kendrick.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
European Search Report from Application No. EP14158818.6 dated May 28, 2014.
Extended European Search Report from Appl. No. EP 16150380.0 dated Mar. 17, 2016.

\* cited by examiner

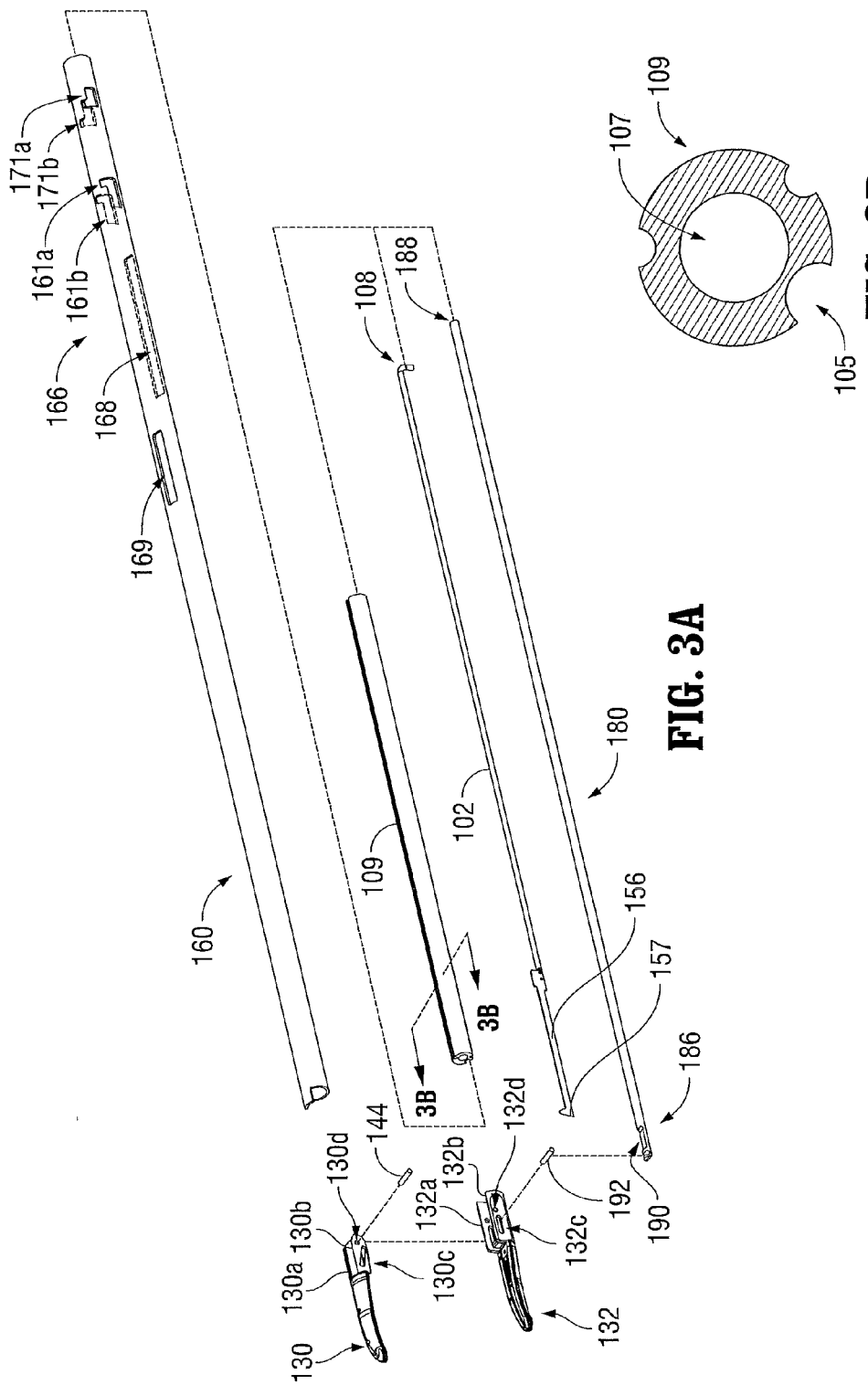

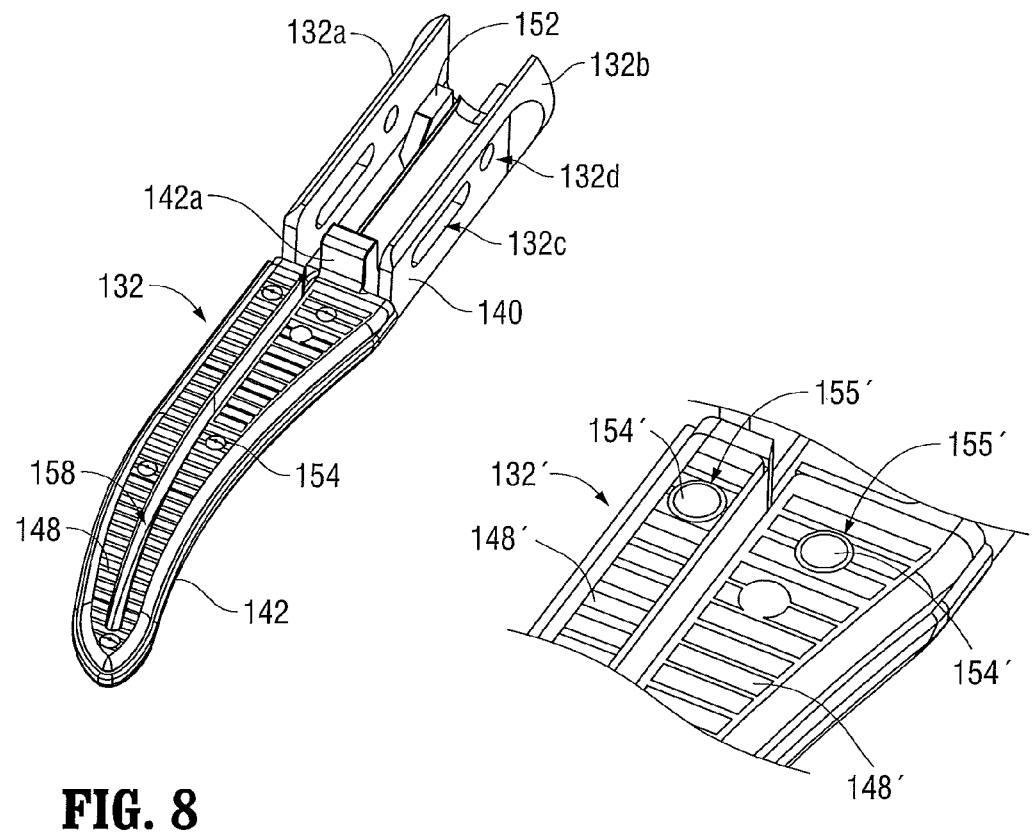
FIG. 8
FIG. 8A
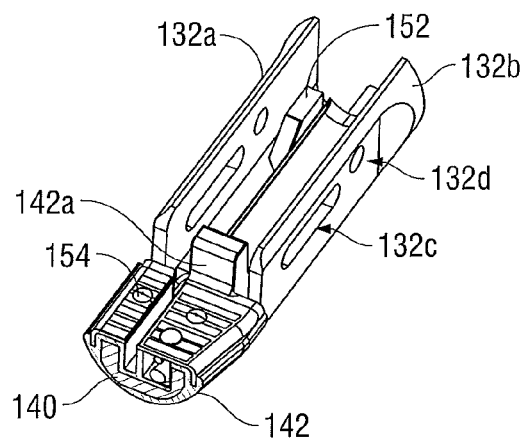
FIG. 9

SURGICAL INSTRUMENT

CROSS-REFERENCE TO RELATED APPLICATIONS

This application claims the benefit of, and priority to, U.S. Provisional Patent Application No. 61/776,136, filed on Mar. 11, 2013, the entire contents of which are hereby incorporated herein by reference.

BACKGROUND

Technical Field

The present disclosure relates generally to the field of surgical instruments. In particular, the disclosure relates to an endoscopic electrosurgical forceps that is economical to manufacture and is capable of sealing and cutting relatively large tissue structures.

Background of Related Art

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaw members. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm$^2$ to about 16 kg/cm$^2$.

SUMMARY

The present disclosure relates to an electrosurgical apparatus and methods for performing electrosurgical procedures. More particularly, the present disclosure relates to electrosurgically sealing tissue.

The present disclosure describes an electrosurgical instrument for treating tissue that is economical to manufacture and is capable of sealing and cutting relatively large tissue structures.

The electrosurgical instrument includes a housing including an elongated shaft having distal and proximal portions. The proximal portion is coupled to the housing. As is traditional, the term "distal" refers herein to an end of the apparatus that is farther from an operator, and the term "proximal" refers herein to the end of the electrosurgical forceps that is closer to the operator.

The elongated shaft defines a longitudinal axis. A stationary actuation member is axially disposed within the elongated shaft and includes a cam pin mechanically coupled to a distal end thereof. An actuating mechanism is operably coupled to the proximal portion of the elongated shaft and is moveable relative to the housing to selectively cause movement of the elongated shaft along the longitudinal axis relative to the stationary actuation member. An end effector includes a pair of opposing first and second jaw members operably coupled about a common pivot such that at least one of the jaw members is movable relative to the other jaw member from a first position wherein the jaw members are disposed in spaced relation relative to one another to a second position wherein the jaw members cooperate to grasp tissue therebetween. At least one of the first and second jaw members includes a camming slot configured to engage the cam pin to move the at least one movable jaw member between the first position and the second position upon movement of the elongated shaft along the longitudinal axis. Each jaw member includes an electrically conductive tissue sealing surface. Each tissue sealing surface is adapted to connect to a source of electrosurgical energy for conducting electrosurgical energy through tissue grasped therebetween to effect a tissue seal. A knife blade is supported in the elongated shaft and is moveable in a longitudinal direction through a knife channel defined along a length of at least one of the jaw members to cut tissue disposed between the jaw members. A switch is supported by the housing and is configured to be engaged by the actuating mechanism to initiate delivery of electrosurgical energy from the electrosurgical energy source to the end effector to treat tissue.

Additionally or alternatively, the switch is operably coupled to a depressible button extending from the housing. The button is configured to be selectively engaged by the actuating mechanism to activate the switch.

Additionally or alternatively, the second jaw member is mechanically coupled to a distal end of the elongated shaft and the first jaw member is configured to move relative to the second jaw member.

Additionally or alternatively, the stationary actuation member includes a longitudinal recess formed along a length thereof. The longitudinal recess is configured to permit movement of the pivot pin in a longitudinal direction upon movement of the elongated shaft.

Additionally or alternatively, the actuation mechanism is configured to engage a mechanical interface disposed within the housing. The mechanical interface is configured to generate a response to engagement with the actuation mechanism upon movement thereof relative to the housing. The mechanical interface may be constructed of a plastic film or the mechanical interface may be constructed of sheet metal. The response may be tactile and/or audible and may correspond to the second position of at least one jaw member. Additionally or alternatively, the response may indicate a position of the actuation mechanism relative to the switch.

Additionally or alternatively, the actuation mechanism includes a handle moveable relative to the housing between a distal position to move at least one jaw member to the first position and a proximal position to move the at least one jaw member to the second position. The handle may engage the switch upon movement of the handle to the proximal position.

Additionally or alternatively, movement of the knife blade in a longitudinal direction is prevented when the handle is in the distal position.

Additionally or alternatively, at least one of the jaw members includes an insulator coupled thereto. The insulator may be configured to electrically insulate the electrically conductive tissue sealing surface from the jaw member. The insulator may form at least one knife blade guide configured to guide the knife into the knife channel.

Additionally or alternatively, the insulator is configured to control splay of at least one of the jaw members.

According to another aspect of the present disclosure, an electrosurgical instrument is provided. The electrosurgical instrument includes a housing and an elongated shaft coupled to the housing and defining a longitudinal axis. An actuating mechanism is operably coupled to the elongated shaft and moveable relative to the housing to selectively cause movement of the elongated shaft along the longitudinal axis. An end effector is supported by the elongated shaft and is adapted for treating tissue. The end effector includes first and second jaw members pivotally coupled to one another to move between open and closed configurations. Each of the jaw members includes a camming surface. A switch is supported by the housing and is configured to be engaged by the actuating mechanism to initiate treatment of tissue. A knife rod extends at least partially through the elongated shaft and is selectively movable in a longitudinal direction. A blade operably coupled to the knife rod is extendable through a knife channel defined along a length of at least one of the jaw members. An inner actuation member extends at least partially through the elongated shaft and the elongated shaft is selectively movable in a longitudinal direction with respect to the knife and with respect to the inner actuation member. The inner actuation member carries a cam pin positioned to engage the camming surface of each of the jaw members to induce the jaw members to move between the open and closed configurations.

According to another aspect of the present disclosure, an electrosurgical system for performing electrosurgery is provided. The electrosurgical system includes an electrosurgical generator configured to provide electrosurgical energy and an electrosurgical instrument. The electrosurgical instrument includes a housing including an elongated shaft having distal and proximal portions. The proximal portion is coupled to the housing. The elongated shaft defines a longitudinal axis. A stationary actuation member is axially disposed within the elongated shaft and includes a cam pin mechanically coupled to a distal end thereof. An actuating mechanism is operably coupled to the proximal portion of the elongated shaft and is moveable relative to the housing to selectively cause movement of the elongated shaft along the longitudinal axis relative to the stationary actuation member. An end effector includes a pair of opposing first and second jaw members operably coupled about a common pivot such that at least one of the jaw members is movable relative to the other jaw member from a first position wherein the jaw members are disposed in spaced relation relative to one another to a second position wherein the jaw members cooperate to grasp tissue therebetween. At least one of the first and second jaw members includes a camming slot configured to engage the cam pin to move the at least one movable jaw member between the first position and the second position upon movement of the elongated shaft along the longitudinal axis. Each jaw member includes an electrically conductive tissue sealing surface. Each tissue sealing surface is configured to connect to the electrosurgical generator for conducting electrosurgical energy through tissue grasped therebetween to effect a tissue seal. A knife blade is supported in the elongated shaft and is moveable in a longitudinal direction through a knife channel defined along a length of at least one of the jaw members to cut tissue disposed between the jaw members. A switch is supported by the housing and is configured to be engaged by the actuating mechanism to initiate delivery of electrosurgical energy from the electrosurgical generator to the end effector to treat tissue.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is a perspective view of the end effector and elongated shaft of FIG. 1 with parts separated;

FIG. 3B is cross-sectional view taken along line 3B-3B of FIG. 3A showing a distal portion of the electrosurgical forceps of FIG. 1 depicting a tube guide;

FIG. 8 is a perspective view of a lower jaw member of the end effector of FIG. 1;

FIG. 8A is an enlarged, perspective view of a portion of another lower jaw member, similar to the lower jaw member of FIG. 8, configured for use with the end effector of FIG. 1;

FIG. 9 is a cross-sectional, perspective view of the lower jaw member of FIG. 8;

DETAILED DESCRIPTION

Figure 1:
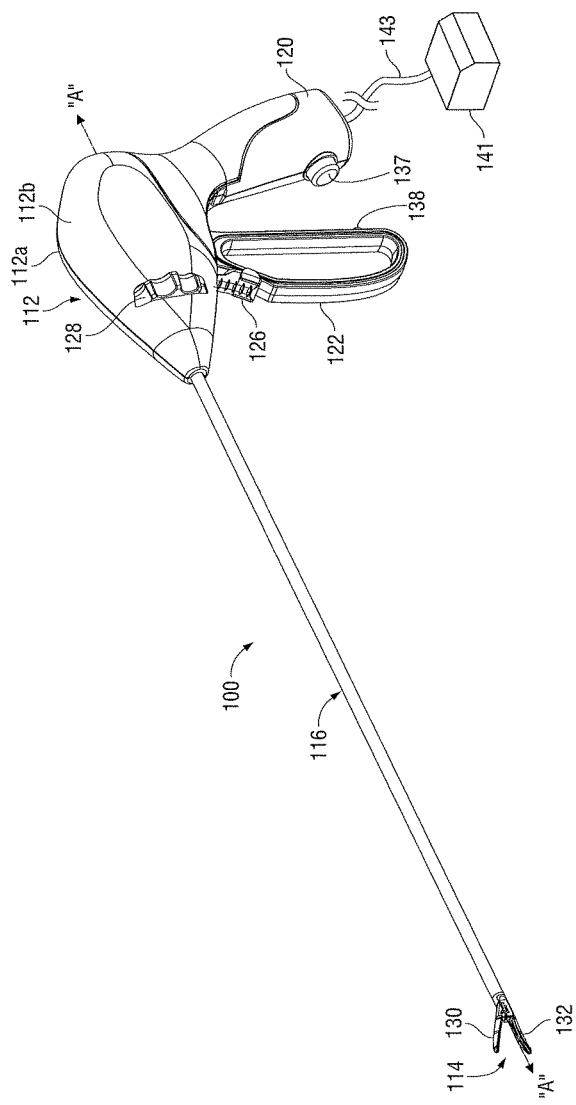
FIG. 1 is a perspective view of an electrosurgical forceps according to an embodiment of the present disclosure including a housing, an elongated shaft, and an end effector.

Referring initially to FIG. 1, an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with endoluminal procedures as well. The housing 112 is constructed of a left housing half 112a and a right housing half 112b. The left and right designation of the housing halves 112a, 112b refer to the respective directions as perceived by an operator using the forceps 100. The housing halves 112a, 112b may be constructed of sturdy plastic, and may be joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (see FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps 114.

To electrically control the end effector 114, the stationary handle 120 supports a depressible button 137 thereon, which is operable by the user to initiate and terminate the delivery of electrosurgical energy to the end effector 114. The depressible button 137 is mechanically coupled to a switch 136 (FIGS. 13A-13D) disposed within the stationary handle 120 and is engageable by a button activation post 138 extending from a proximal side of the moveable handle 122 upon proximal movement of the moveable handle 122 to an actuated or proximal position (FIG. 13C). The switch 136 is in electrical communication with an electrosurgical generator 141 via suitable electrical wiring (not explicitly referenced) extending from the housing 112 through a cable 143 extending between the housing 112 and the electrosurgical generator 141. The generator 141 may include devices such as the LigaSure® Vessel Sealing Generator and the Force-Triad® Generator sold by Covidien. The cable 143 may include a connector (not shown) thereon such that the forceps 100 may be selectively coupled electrically to the generator 141.

Referring now to FIGS. 2A-3A, the end effector 114 may be moved from the open configuration (FIG. 2A) wherein tissue (not shown) is received between the jaw members 130, 132, and the closed configuration (FIG. 2B), wherein the tissue is clamped and treated. The jaw members 130, 132 pivot about a pivot pin 144 to move the end effector 114 to the closed configuration of FIG. 2B wherein the sealing plates 148, 150 provide a pressure to tissue grasped therebetween. In some embodiments, to provide an effective tissue seal, a pressure within a range between about 3 $kg/cm^2$ to about 16 $kg/cm^2$ and, desirably, within a working range of about 7 $kg/cm^2$ to about 13 $kg/cm^2$, may be applied to the tissue. Also, in the closed configuration, a separation or gap distance is maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 inches to about 0.005 inches, may be provided. In some embodiments, the stop members 154 are constructed of a heat-resistant ceramic deposited onto the jaw members 130, 132. In other embodiments, the stop members 154 are constructed of an electrically non-conductive plastic molded onto the jaw members 130, 132, e.g., by a process such as overmolding or injection molding. The stop members 154 may define any suitable number, arrangement, and/or configuration, depending on a particular purpose.

Referring momentarily to FIG. 8A, another embodiment of a lower jaw member 132' is shown. Lower jaw member 132' is similar to lower jaw member 132 (FIGS. 2A-3A) except as detailed below. Lower jaw member 132' includes a sealing plate 148' having a plurality of stop members 154' disposed thereon in any suitable configuration. A wetting ring 155' defined within the sealing plate 148' is disposed about each of the stop members 154'. Wetting rings 155' may be formed via etching or other suitable process and are formed on sealing plate 148' prior to depositing (or otherwise forming) the stop members 154'. Upon depositing the ceramic onto sealing plate 148' to form the stop members 154' (or prior to otherwise forming the stop members 154'), wetting rings 155' facilitate the formation of each of the stop members 154' in a particular shape, e.g., circular, thus providing greater shape uniformity among the plurality of stop members 154'.

Referring again to FIGS. 2A-3A, the upper and lower jaw members 130, 132 are electrically coupled to cable 143, and thus to the generator 141 (e.g., via respective suitable electrical wiring extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130. In some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150 to tissue. Alternatively, the sealing plates 148 and 150 may be configured to deliver monopolar energy to tissue. In a monopolar configuration, one or both sealing plates 148 and 150 deliver electrosurgical energy from an active terminal, e.g., (+), while a return pad (not shown) is placed generally on a patient and provides a return path to the opposite terminal, e.g., (−), of the generator 141. Each jaw member 130, 132 includes a jaw insert 140 and an insulator 142 that serves to electrically insulate the sealing plates 150, 148 from the jaw insert 140 of the jaw members 130, 132, respectively.

Figure 2A:
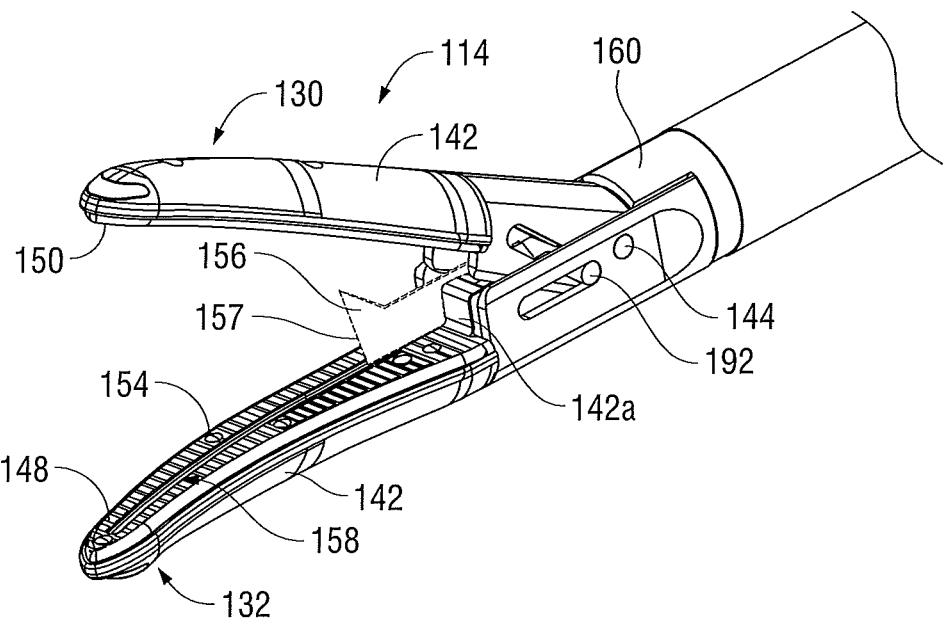
FIG. 2A is an enlarged, perspective view of the end effector of FIG. 1 depicted with a pair of jaw members in an open configuration.

Electrosurgical energy may be delivered to the tissue through the electrically conductive seal plates 148, 150 to effect a tissue seal. Once a tissue seal is established, a knife blade 156 having a sharpened distal edge 157 may be advanced through a knife channel 158 defined in one or both jaw members 130, 132 to transect the sealed tissue. Although the knife blade 156 is depicted in FIG. 2A as extending from the elongated shaft 116 when the end effector 114 is in an open configuration, in some embodiments, extension of the knife blade 156 into the knife channel 158 when the end effector 114 is in the open configuration is prevented, as discussed below with reference to FIGS. 13A-13D.

Referring to FIG. 3A, the elongated shaft 116 includes various longitudinal components that operatively couple the end effector 114 to the various actuators supported by the housing 112 (FIG. 1). An outer shaft member 160 defines an exterior surface of the elongated shaft 116 and houses other components therein as described below. The outer shaft member 160 is configured for longitudinal motion with respect to an inner actuation member 180 axially received within the outer shaft member 160. The inner actuation member 180 may be a rod, a shaft, a tube, folded metal, stamped metal, or other suitable structure. A proximal portion 166 of the outer shaft member 160 is configured for receipt within the housing 112 (FIG. 1), and includes features for operatively coupling the outer shaft member 160 to various elements of the housing 112. More specifically, the proximal portion 166 of the outer shaft member 160 includes, in order from distal to proximal, a longitudinal slot 169 to couple the outer shaft member 160 to the rotation knob 128, a longitudinal knife slot 168 defined therethrough, a pair of opposing distal locking slots 161a, 161b, and a pair of opposing proximal locking slots 171a, 171b. The connection established between the outer shaft member 160 and the rotation knob 128 is described below with reference to FIG. 4.

Figure 10:
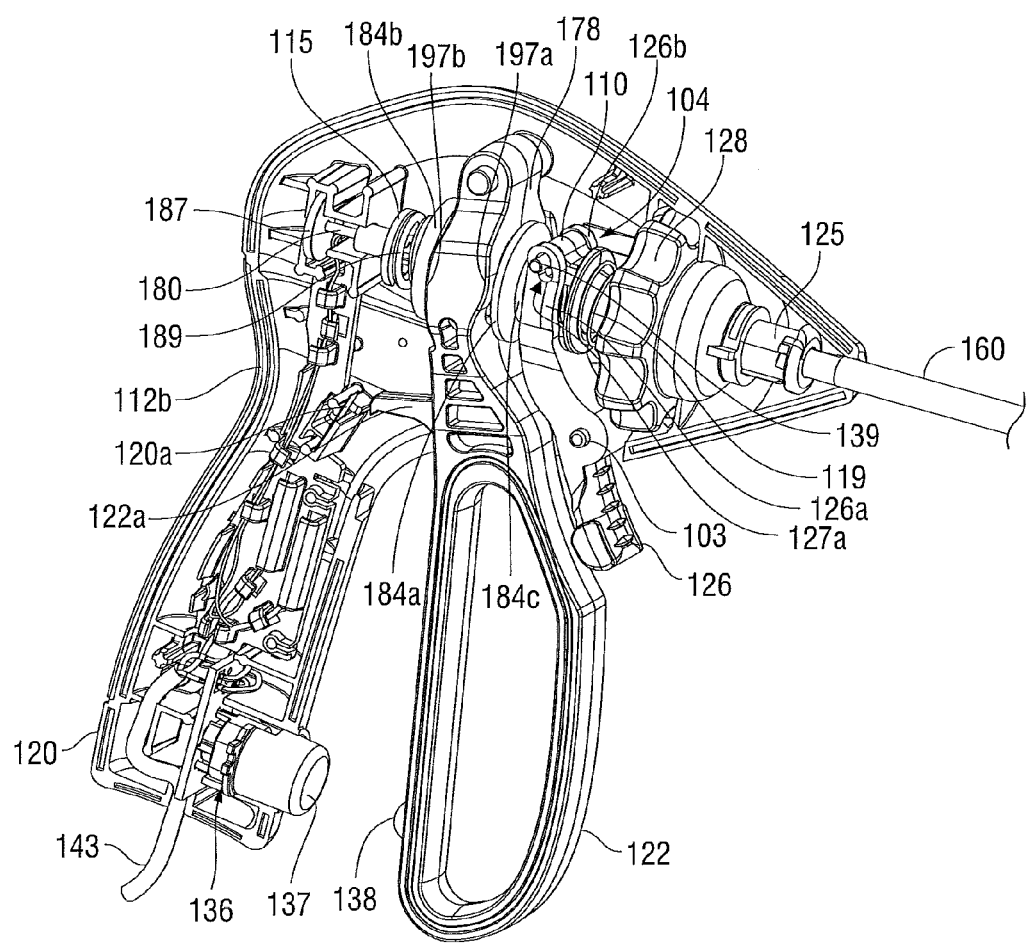
FIG. 10 is a perspective view of a proximal portion of the instrument of FIG. 1 with a portion of the housing removed revealing internal components.

A distal portion 186 of the inner actuation member 180 includes a longitudinal recess 190 defined therein that provides clearance for the pivot pin 144 and thus, permits longitudinal reciprocation of the pivot pin 144 (via longitudinal reciprocation of the outer shaft member 160) independent of the inner actuation member 180. Distally of the longitudinal recess 190, a cam pin 192 is mechanically coupled (e.g., via welding, friction-fit, laser welding, etc) to the distal portion 186 of the inner actuation member 180. A proximal portion 188 of the inner actuation member 180 includes a washer 187 coupled thereto (FIG. 10). The washer 187 is captured within the housing 112 and serves to prohibit longitudinal motion of the inner actuation member 180 parallel to the longitudinal axis A-A.

Figure 2B:
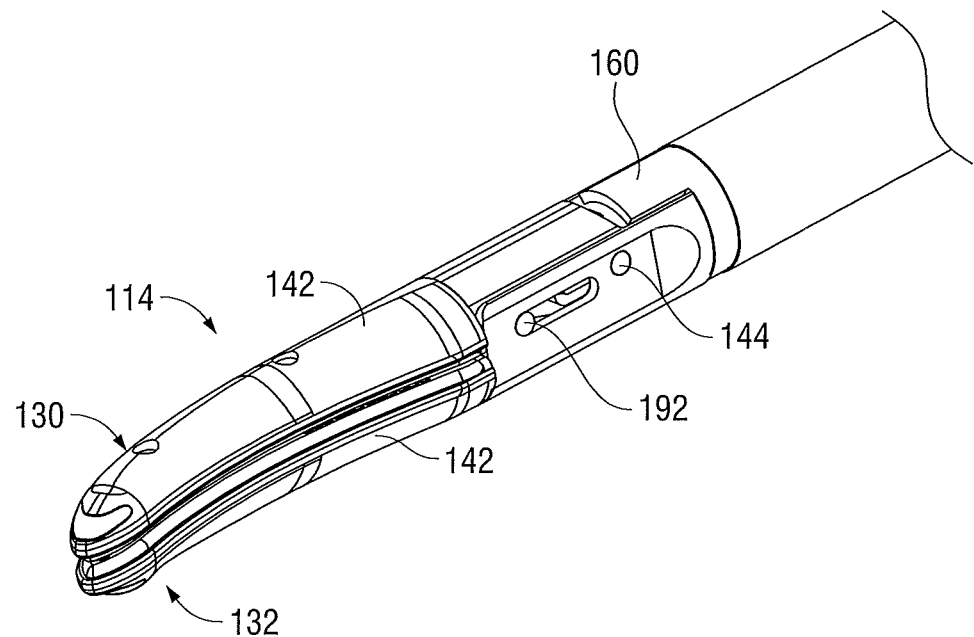
FIG. 2B is an enlarged, perspective view of the end effector of FIG. 1 depicted with the pair of jaw members in a closed configuration.

The pivot pin 144 extends through a proximal portion of each of the jaw members 130, 132 to pivotally support the jaw members 130, 132 at the distal end of the inner actuation member 180. A proximal portion of each of the jaw members 130, 132 includes two laterally spaced parallel flanges or "flags" 130a, 130b and 132a, 132b respectively, extending proximally from a distal portion of the jaw members 130 and 132 (FIGS. 3A, 5, and 7-9). A lateral cam slot 130c and a lateral pivot bore 130d extend through each of the flags 130a, 130b of the upper jaw member 130 (FIG. 3A). Similarly, a lateral cam slot 132c and a lateral pivot bore 132d extend through each of the flags 132a, 132b of the lower jaw member 132 (FIGS. 8 and 9). The pivot bores 130d, 132d receive the pivot pin 144 in a slip-fit relation that permits the jaw members 130, 132 to pivot about the pivot pin 144 to move the end effector 114 between the open and closed configurations (FIGS. 2A and 2B, respectively).

A knife rod 102 is coupled (e.g., via welding) at a distal-most end to the sharpened knife blade 156 and includes an angled proximal end 108 that provides a mechanism for operatively coupling the knife rod 102 to the trigger 126. In some embodiments, the angled proximal end 108 of the knife rod 102 is formed by bending the knife rod 102 ninety degrees at its proximal end during manufacturing. The connection between the knife rod 102 and the trigger 126 is described in detail below with reference to FIGS. 10, 11, 12A, and 12B. The sharpened distal edge 157 of the knife blade 156 may be applied to the distal end of the knife blade 156 using a variety of manufacturing techniques such as, for example, grinding, coining, electrochemical etching, electropolishing, or other suitable manufacturing technique, for forming sharpened edges.

Referring to FIGS. 3A and 3B, a tube guide 109 is disposed within the outer shaft member 160 and includes a lumen 107 axially disposed therethrough. The inner actuation member 180 is received within the guide lumen 107, which serves to orient and align the inner actuation member 180 within the outer shaft member 160. The knife rod 102 is received within a longitudinal guide recess 105 formed in the outer surface of the guide tube 109. The guide recess 105 serves to guide longitudinal motion of the knife rod 102 within the outer shaft member 160 and to radially space the knife rod 102 from the inner actuation member 180 to prevent the inner actuation member 180 from interfering with reciprocal motion of the knife rod 102.

Figure 3C:
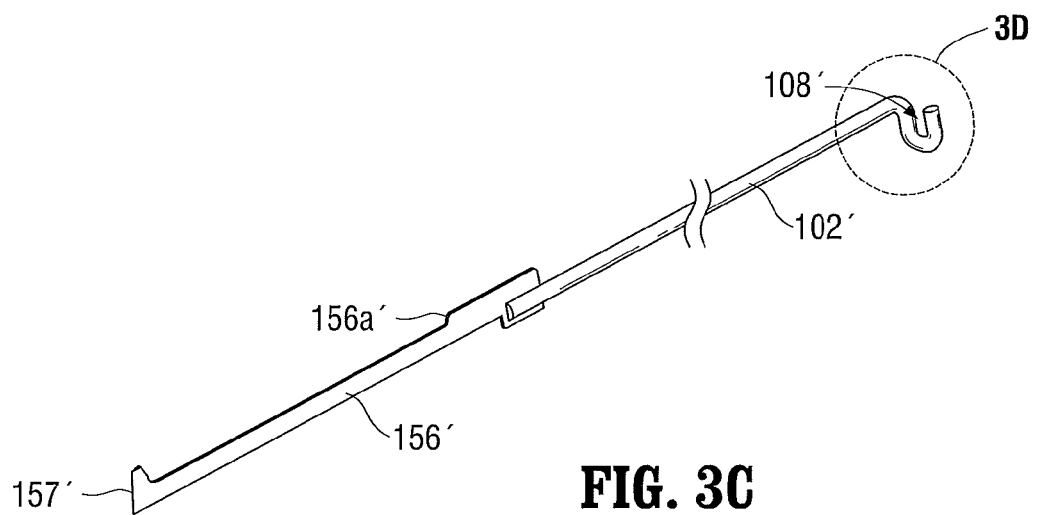
FIG. 3C is a perspective view of another knife blade and knife bar configuration for use with the end effector and elongated shaft of FIG. 1.
Figure 4:
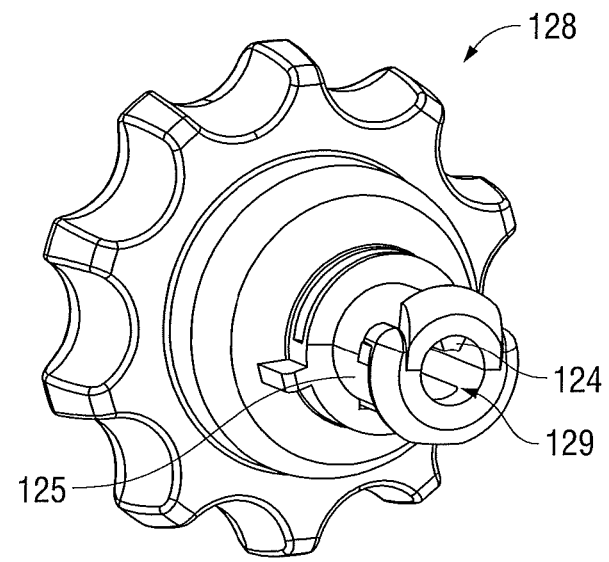
FIG. 4 is a proximally-facing, perspective view of a rotation knob depicting a passageway for receiving the elongated shaft of FIG. 1.

Referring now to FIG. 4, the rotation knob 128 includes a distal portion 125 extending distally therefrom and a passageway 129 defined therethrough for receiving the outer shaft member 160. The passageway 129 has a generally circular profile corresponding to the circular profile of the outer shaft member 160. The passageway 129 includes a longitudinal keying member 124 that is configured to align with and be seated within longitudinal slot 169 (FIG. 3A) of the outer shaft member 160. The keying member 124 projects laterally inward along the length of passageway 129 such that the insertion of the outer shaft member 160 into the passageway 129 of the rotation knob 128 operatively couples the outer shaft member 160 to the rotation knob 128. Rotational motion imparted to the rotation knob 128 may thus impart rotational motion to each of the components of the elongated shaft 116, and to the end effector 114, which is coupled thereto. As shown in FIGS. 10, 11, and 13A-13D, the rotation knob 128 is supported in the housing 112 and, as shown in FIG. 1, extends radially outward from opposing sides of the housing 112 (only shown extending radially outward from housing half 112b).

Figure 5:
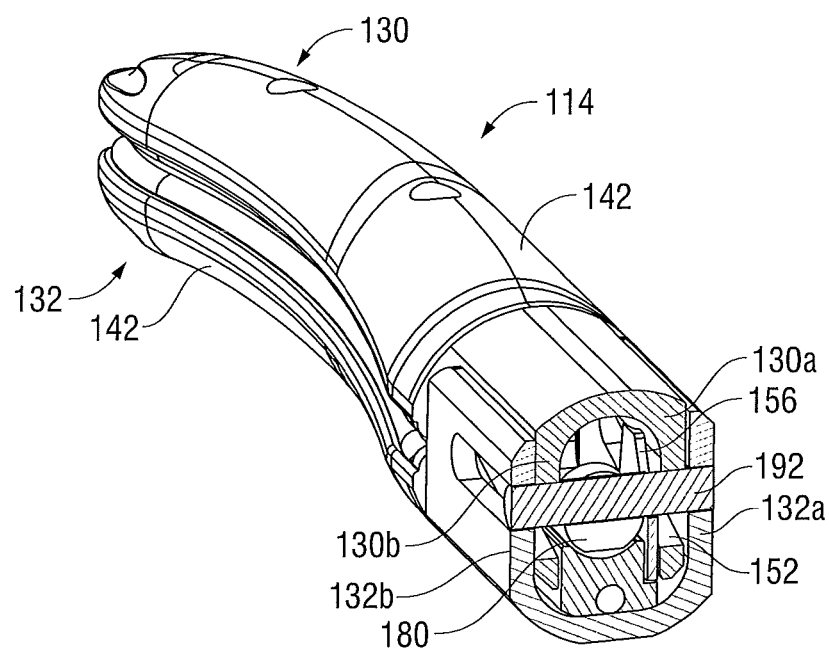
FIG. 5 is a cross-sectional, perspective view of the end effector of FIG. 1.

Referring now to FIG. 5, the end effector 114 is coupled to the distal end of the inner actuation member 180 by the cam pin 192. The cam pin 192 represents a longitudinally stationary reference for longitudinal movement of the outer shaft member 160 and the knife rod 102. The cam pin 192 extends through the flags 132a, 132b of the lower jaw member 132 and the flags 130a and 130b of the upper jaw member 130.

Figure 6:
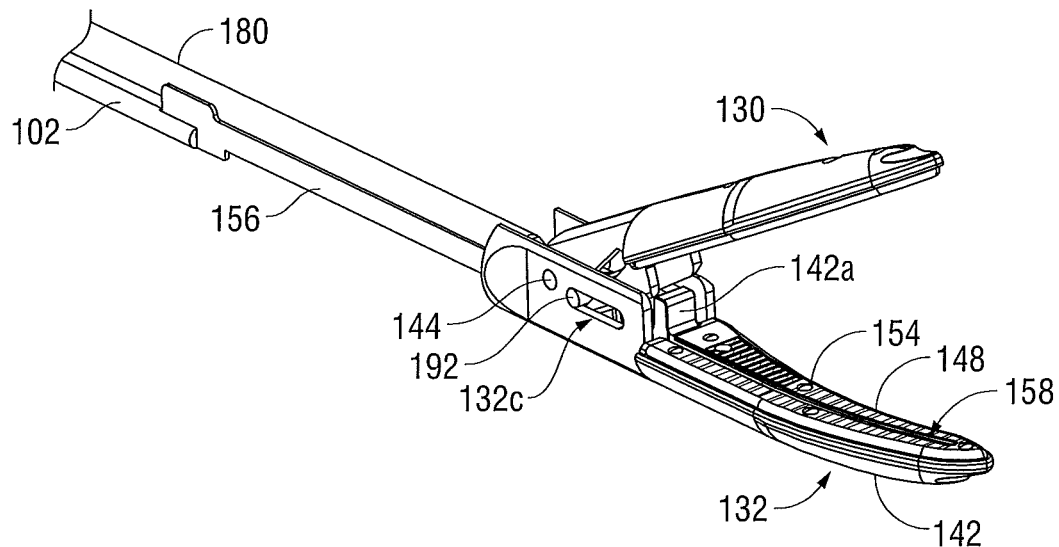
FIG. 6 is a partial, proximal-facing perspective view of a distal portion of a jaw actuation mechanism of the end effector of FIG. 1.

Referring now to FIG. 6, the end effector 114 is shown in the open configuration. Since the inner actuation member 180 is coupled to the cam pin 192, when the outer shaft member 160 (removed from view in FIG. 6 for clarity) is in an unactuated or distal position such that the inner actuation member 180 is in a proximal position relative to the outer shaft member 160, the cam pin 192 is located in a proximal position in cam slots 130c and 132c defined through the flags 130a, 130b, 132a, 132b of the jaw members 130, 132, respectively.

The outer shaft member 160 may be drawn proximally relative to the inner actuation member 180 and the cam pin 192 to move the end effector 114 to the closed configuration (see FIG. 2B). Since the longitudinal position of the cam pin 192 is fixed, and since the cam slot 130c is obliquely arranged with respect to the longitudinal axis A-A, proximal retraction of the outer shaft member 160 induces distal translation of the cam pin 192 through the cam slots 130c, 132c such that the jaw member 130 pivots toward jaw member 132 about the pivot pin 144. Conversely, when the end effector 114 is in the closed configuration, longitudinal translation of the outer shaft member 160 in a distal direction induces proximal translation of the cam pin 192 through the cam slots 130c, 132c such that jaw member 130 pivots away from jaw member 132 toward the open configuration.

In some embodiments, the inner actuation member 180 may be configured to move relative to the outer shaft member 160 to move the end effector 114 between the open and closed configurations. In this scenario, the moveable handle 122 may be operably coupled to the inner actuation member 180 and the washer 187 coupled to the proximal portion 188 of the inner actuation member 180 may be removed such that the inner shaft member 180 is free to move longitudinally along the longitudinal axis A-A upon actuation of the moveable handle 122. Proximal retraction of the inner actuation member 180 may induce proximal translation of the cam pin 192 through the cam slots 130c, 132c such that the jaw member 130 pivots away from jaw member 132 about the pivot pin 144 toward the open configuration. Conversely, when the end effector 114 is in the open configuration, longitudinal translation of the inner actuation member 180 in a distal direction induces distal translation of the cam pin 192 through the cam slots 130c, 132c such that jaw member 130 pivots toward jaw member 132 toward the closed configuration.

Figure 7:
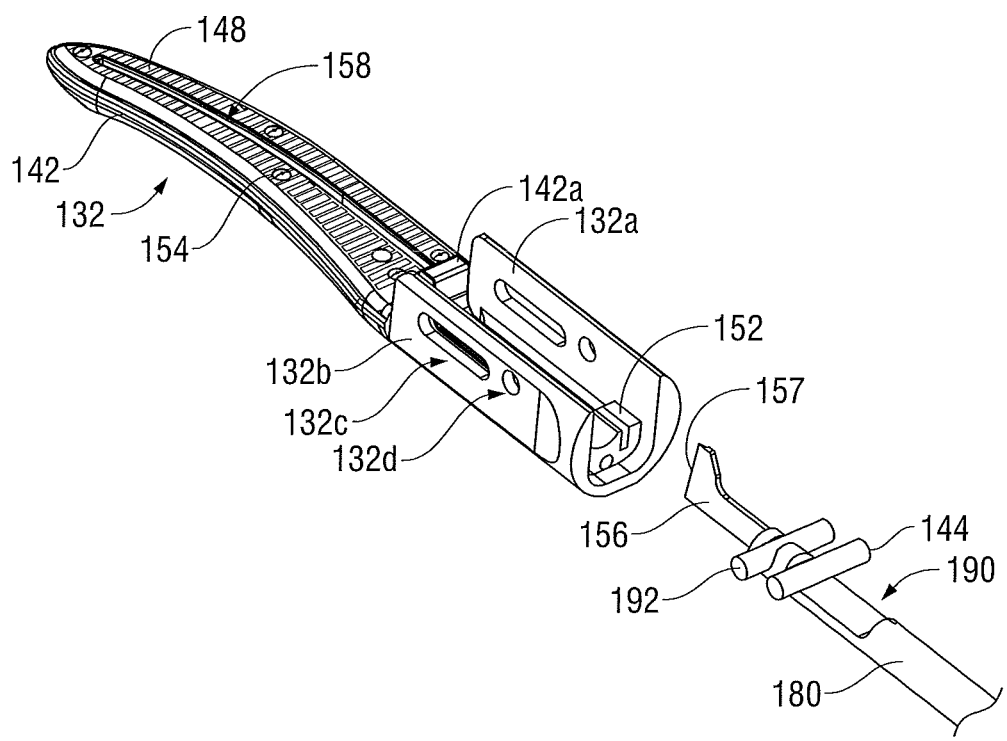
FIG. 7 is a partial, distal-facing perspective view of distal portion of a knife actuation mechanism of the end effector of FIG. 1.

Referring now to FIG. 7, the pins 144, 192 do not interfere with the reciprocal motion of the knife blade 156. A proximal portion of the insulator 142 forms a blade guide 152 (also see FIGS. 5, 8, and 9) that serves to align the knife blade 156 such that the knife blade 156 readily enters the knife channel 158 defined in the jaw members 130, 132 (jaw member 130 removed from view in FIG. 7 for clarity).

Referring now to FIGS. 8 and 9, the lower jaw member 132 is constructed of three major components: the jaw insert 140, the insulator 142, and the sealing plate 148. The flags 132a, 132b of the jaw member 132 define a proximal portion of the jaw insert 140 and a generally u-shaped profile of the jaw insert 140 extends distally to support the tissue engaging portion of the jaw member 132. Upper jaw member 130 includes the same three major components as lower jaw member 132, including sealing plate 150, jaw insert 140, and insulator 142, and is constructed in the same manner as lower jaw member 132. However, lower jaw member 132 is fixedly engaged, e.g., welded, to outer shaft member 160, while upper jaw member 130 is pivotable relative to lower jaw member 132 and outer shaft member 160 between the open and closed configurations. In order to facilitate alignment of lower jaw member 132 and, more particularly, jaw insert 140 of lower jaw member 132, with outer shaft member 160 during welding (or other suitable fixed engagement), jaw insert 140 and outer shaft member 160 may include complementary alignment features, e.g., a complementary recess (not explicitly shown) defined within jaw insert 140 and a complementary protrusion (not explicitly shown) extending from outer shaft member 160. As an alternative to the unilateral configuration detailed above, both of the upper and lower jaw members 130, 132, respectively, may be pivotable relative to one another and outer shaft member 160, thus defining a bilateral configuration.

The insulator 142 of jaw members 130, 132 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The insulator 142 may be overmolded onto the jaw insert 140 in either a single-shot or a two-shot injection molding process such that each of the sealing plates 148, 150 are coupled to and in spaced relation with their respective jaw inserts 140. Additionally or alternatively, the insulator 142 may be mechanically coupled to the jaw insert 140, e.g., pressed, snapped, glued, etc. Various features may be molded into the insulator 142 that facilitate the attachment of the sealing plates 148, 150 to the jaw inserts 140. For example, tabs may be provided that permit a snap-fit attachment, or ridges may be formed that permit ultrasonic welding of the sealing plates 148, 150 onto the insulators 142. In some embodiments, the insulator 142 on the lower jaw member 132 forms a tissue stop 142a extending therefrom adjacent to the knife channel 158 and proximal to the sealing plate 148. The tissue stop 142a serves to prevent tissue from entering the distal end of the outer shaft member 160 and to prevent splay of the flags 130a, 130b of the upper jaw member 130. In some embodiments, the tissue stop 142a may be formed by the insulator 142 on the upper jaw member 130 or on both the upper jaw member 130 and the lower jaw member 132. The tissue stop 142a may also serve to align the knife blade 156 as the knife blade 156 enters the knife channel 158 defined in the jaw members 130, 132. To this end, the surface of the tissue stop 142a extending along the path of the knife blade 156 may define a chamfered configuration to further facilitate alignment of the knife blade 156 as the knife blade 156 enters the knife channel 158.

Referring now to FIG. 10, the connection of the movable handle 122 and the knife trigger 126 to the longitudinally movable components of the elongated shaft 116 is described. The movable handle 122 may be manipulated to impart longitudinal motion to the outer shaft member 160, and the knife trigger 126 may be manipulated to impart longitudinal motion to the knife rod 102. As discussed above, longitudinal motion of the outer shaft member 160 serves to move the end effector 114 between the open configuration of FIG. 2A and the closed configuration of FIG. 2B, and longitudinal motion of the knife rod 102 serves to move knife blade 156 through knife channel 158 (FIG. 2A).

Figure 11:
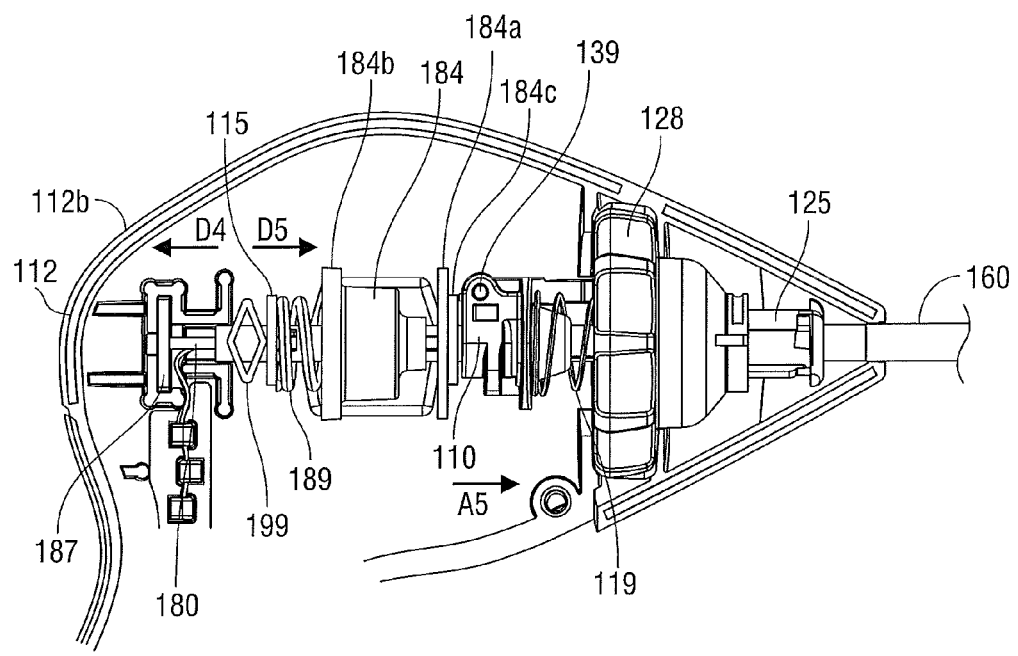
FIG. 11 is a partial, side view of a proximal portion of the instrument of FIG. 1.

The movable handle 122 is operatively coupled to the outer shaft member 160 by a clevis 178 defined at an upper end of the movable handle 122. The clevis 178 is pivotally supported on the housing 112. The clevis 178 extends upwardly about opposing sides of a drive collar 184 (FIG. 11) supported on the outer shaft member 160 and includes rounded drive surfaces 197a and 197b thereon. Drive surface 197a engages a proximal-facing surface of a distal spring washer 184a and drive surface 197b engages a distal facing surface of a proximal rim 184b of the drive collar 184 (FIG. 11). The distal spring washer 184a engages a proximal facing surface of a distal spring stop 184c that, in turn, engages the opposing distal locking slots 161a, 161b (FIG. 3A) extending through the proximal portion 166 (FIG. 3A) of the outer shaft member 160 to couple the distal spring stop 184c to the outer shaft member 160. The drive surfaces 197a, 197b are arranged along the longitudinal axis A-A such that pivotal motion of the movable handle 122 induces corresponding longitudinal motion of the drive collar 184 (FIG. 11) along the longitudinal axis A-A.

Referring now to FIG. 11, proximal longitudinal motion may be imparted to the outer shaft member 160 by pushing the proximal rim 184b of the drive collar 184 proximally with the movable handle 122 (FIG. 10) as indicated by arrow D4 (FIG. 11). A spring 189 is constrained between a proximal facing surface of the drive collar 184 and a proximal spring stop 115. The proximal spring stop 115 engages the opposing proximal locking slots 171a, 171b (FIG. 3A) extending through the proximal portion 166 (FIG. 3A) of the outer shaft member 160 to couple the proximal spring stop 115 to the outer shaft member 160. Thus, the proximal spring stop 115 serves as a proximal stop against which spring 189 compresses.

Distal longitudinal motion is imparted to the outer shaft member 160 by driving the drive collar 184 distally with the movable handle 122 (FIG. 10). Distal longitudinal motion of the drive collar 184 induces a corresponding distal motion of the outer shaft member 160 by virtue of the coupling of the drive collar 184 to opposing distal locking slots 181a, 181b extending through the proximal portion 166 of the outer shaft member 160 (FIG. 3A). In some embodiments, a kick-out spring 199 is positioned between proximal spring stop 115 and a portion of housing 112 to ensure full return of outer shaft member 160 distally upon release or return of movable handle 122 (FIG. 10). The kick-out spring 199 may include a pair of plate surfaces interconnected via living hinges, as shown, although any other suitable spring may be provided.

Proximal longitudinal motion of the outer shaft member 160 draws jaw member 132 proximally such that the cam pin 192 advances distally to pivot jaw member 130 toward jaw member 132 to move the end effector 114 to the closed configuration as described above with reference to FIG. 6. Once the jaw members 130 and 132 are closed, the outer shaft member 160 essentially bottoms out (i.e., further proximal movement of the outer shaft member 160 is prohibited since the jaw members 130, 132 contact one another). Further proximal movement of the movable handle 122 (FIG. 10), however, will continue to move the drive collar 184 proximally. This continued proximal movement of the drive collar 184 further compresses the spring 189 to impart additional force to the outer shaft member 160, which results in additional closure force applied to tissue grasped between the jaw members 130, 132 (see FIG. 2B).

Referring again to FIG. 10, the trigger 126 is pivotally supported in the housing 112 about a pivot boss 103 protruding from the trigger 126. The trigger 126 is operatively coupled to the knife rod 102 by a knife connection mechanism 104 such that pivotal motion of the trigger 126 induces longitudinal motion of the knife rod 102. The knife connection mechanism 104 includes upper flanges 126a, 126b of the trigger 126 and a knife collar 110.

Figure 3D:
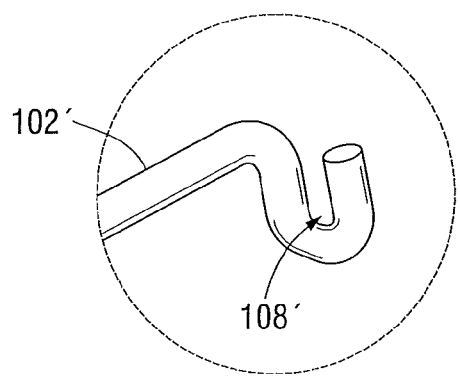
FIG. 3D is an enlarged, perspective view of the area of detail indicated in FIG. 3C.
Figure 3E:
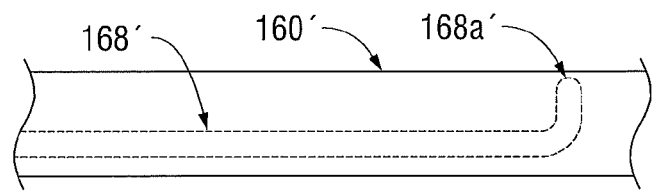
FIG. 3E is a perspective view of a portion of another elongated shaft, similar to the elongated shaft of FIG. 1, configured for use with the end effector of FIG. 1.
Figure 12A:
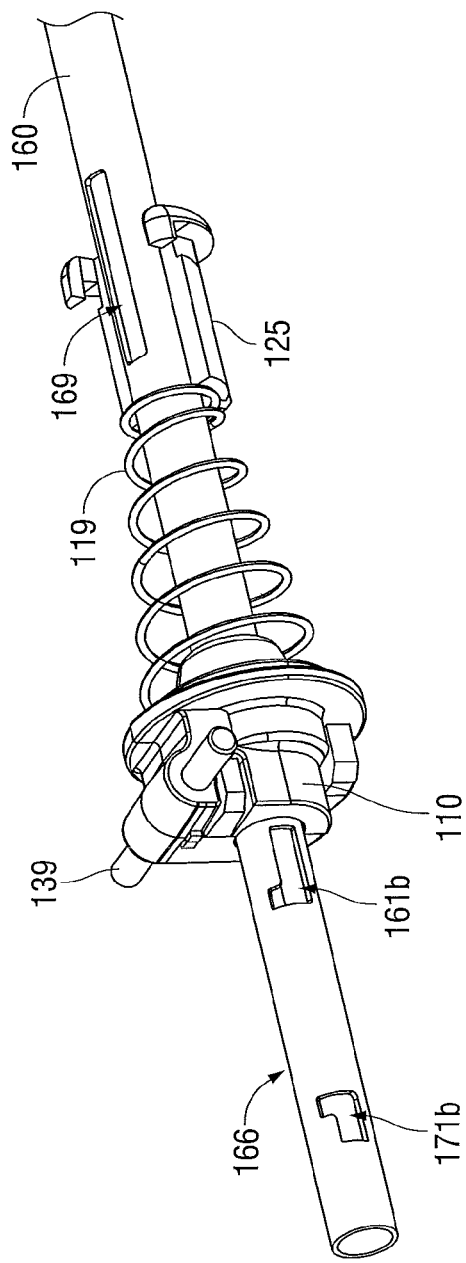
FIG. 12A is a perspective view of a proximal portion of the knife actuation mechanism of the end effector of FIG. 1.
Figure 12B:
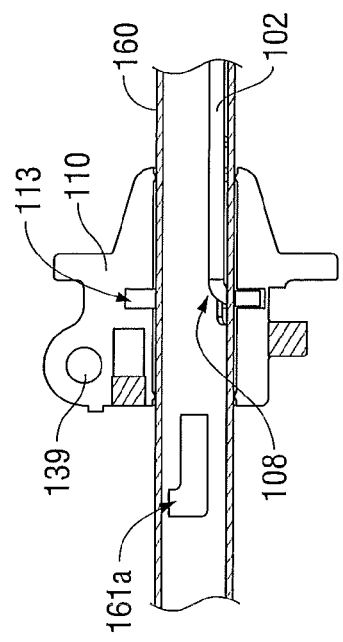
FIG. 12B is a cross-sectional, side view of a knife collar of the knife actuation mechanism of the end effector of FIG. 1.

Referring now to FIGS. 11, 12A, and 12B, the knife collar 110 includes a pair of integrally formed pin bosses 139a, 139b extending from opposing sides thereof. As shown by FIG. 12B, the knife collar 110 includes an interior circular channel 113 that captures the angled proximal end 108 of the knife rod 102 to couple the knife rod 102 to the knife collar 110. Referring momentarily to FIGS. 3C and 3D, in conjunction with FIG. 12B, in some embodiments, the proximal end 108' of the knife rod 102' may alternatively define a hooked configuration to help further inhibit disengagement of the proximal end 108' of the knife rod 102' from within the channel 113 of the knife collar 110. In such embodiments, as shown in FIG. 3E, the knife slot 168' defined within the outer shaft member 160' further includes an angled portion 168a' disposed at the proximal end thereof to accommodate the hooked proximal end 108' of the knife rod 102'.

Referring again to FIGS. 11, 12A, and 12B, upon longitudinal motion of the outer shaft member 160, the angled proximal end 108 of the knife rod 102 translates longitudinally within knife slot 168 (FIG. 3A) of the outer shaft member 160 such that the longitudinal motion of outer shaft member 160 is unimpeded by the angled proximal end 108 of the knife rod 102. Upon rotation of the elongated shaft 116 and end effector 114 about the longitudinal axis A-A via the rotation knob 128 (FIG. 1), the angled proximal end 108 of the knife rod 102 freely rotates within the interior circular channel 113 of the knife collar 110 such that the outer and inner actuation members 160 and 180 (removed from view in FIG. 12B for clarity), and the knife rod 102 rotate within the knife collar 110 about the longitudinal axis A-A. In this way, the knife collar 110 serves as a stationary reference for the rotational movement of the outer shaft member 160, the inner actuation member 180, and the knife rod 102.

Referring again to FIG. 10, the upper flanges 126a, 126b of the trigger 126 include respective slots 127a, 127b defined therethrough that are configured to receive the pin bosses 139a, 139b, respectively, of the knife collar 110 such that pivotal motion of the trigger 126 induces longitudinal motion of the knife collar 110 and, thus, the knife rod 102 by virtue of the coupling of knife rod 102 to the knife collar 110.

Referring now to FIGS. 11 and 12A, when the trigger 126 is moved to induce motion of the knife collar 110 in order to translate the blade 156 through the knife channel 158, the knife collar 110 translates along the outer shaft member 160 in the direction of arrow A5 to abut a spring 119 such that spring 119 compresses against the distal portion 125 of the rotation knob 128 (FIG. 12A). The spring 119 biases the knife collar 110 proximally along the outer shaft member 160. With reference to FIG. 3C, in some embodiments, a hard stop 156a' formed at the proximal end of knife blade 156' is provided for interference with the pivot pin 144 of end effector 114 (FIG. 2B) to limit the travel distance, e.g., extension, of knife blade 156'.

Figure 13A:
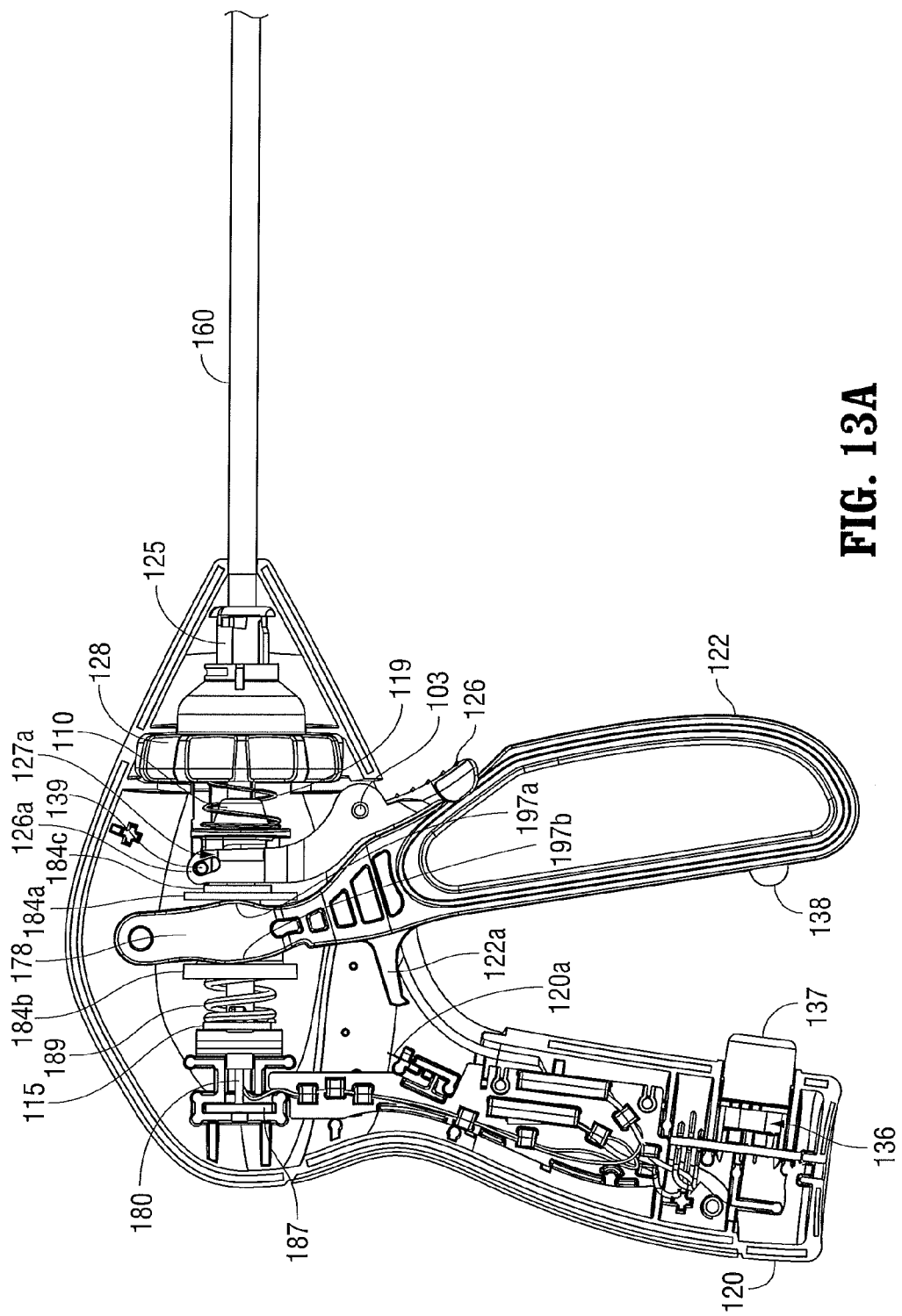
FIG. 13A is a side view of the proximal portion of the instrument of FIG. 10 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members.
Figure 13B:
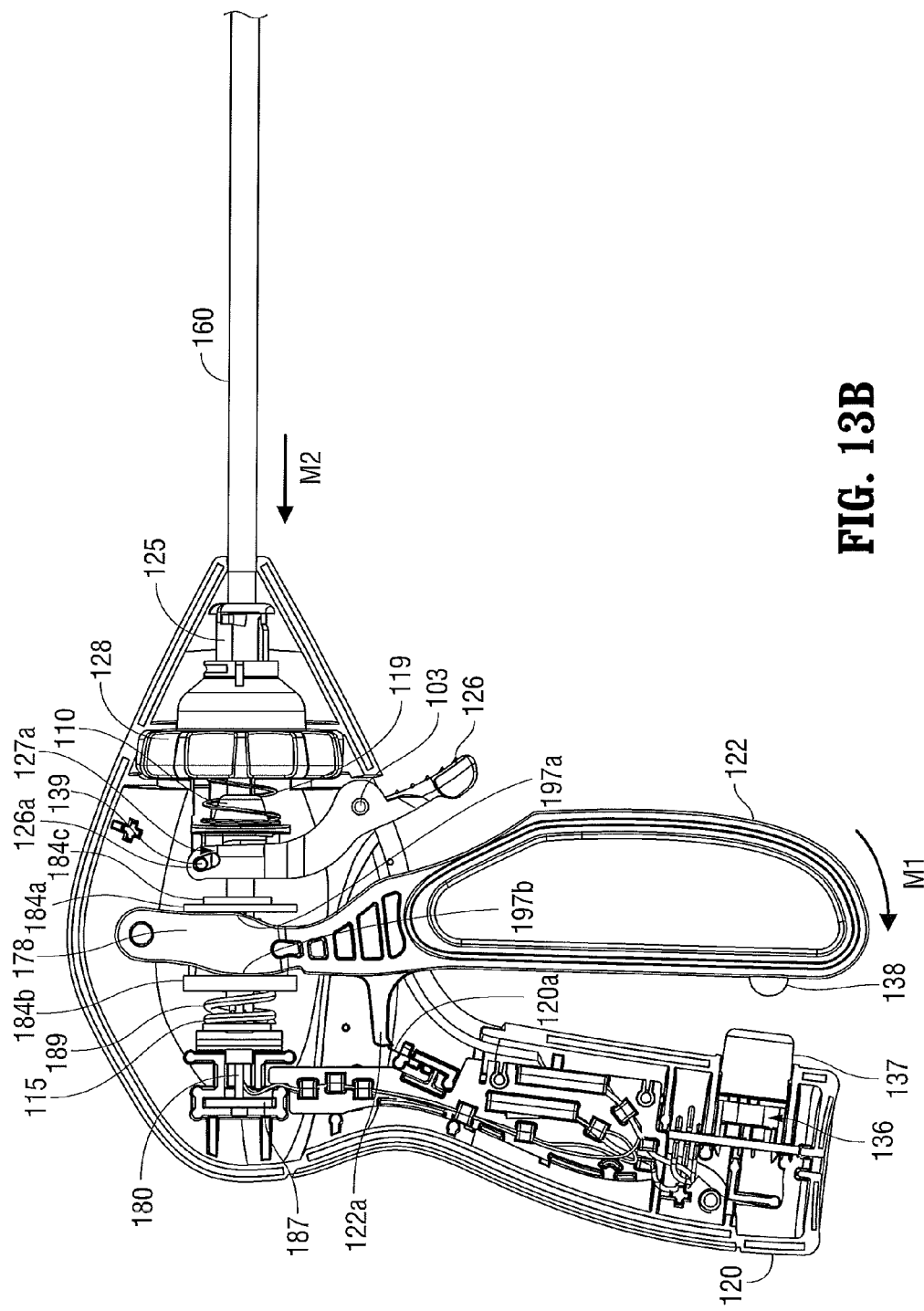
FIG. 13B is a side view of the proximal portion of the instrument of FIG. 10 depicting the movable handle in an intermediate position with respect to the stationary handle, which corresponds to a first closed configuration of the end effector wherein the jaw members encounter one another.
Figure 13C:
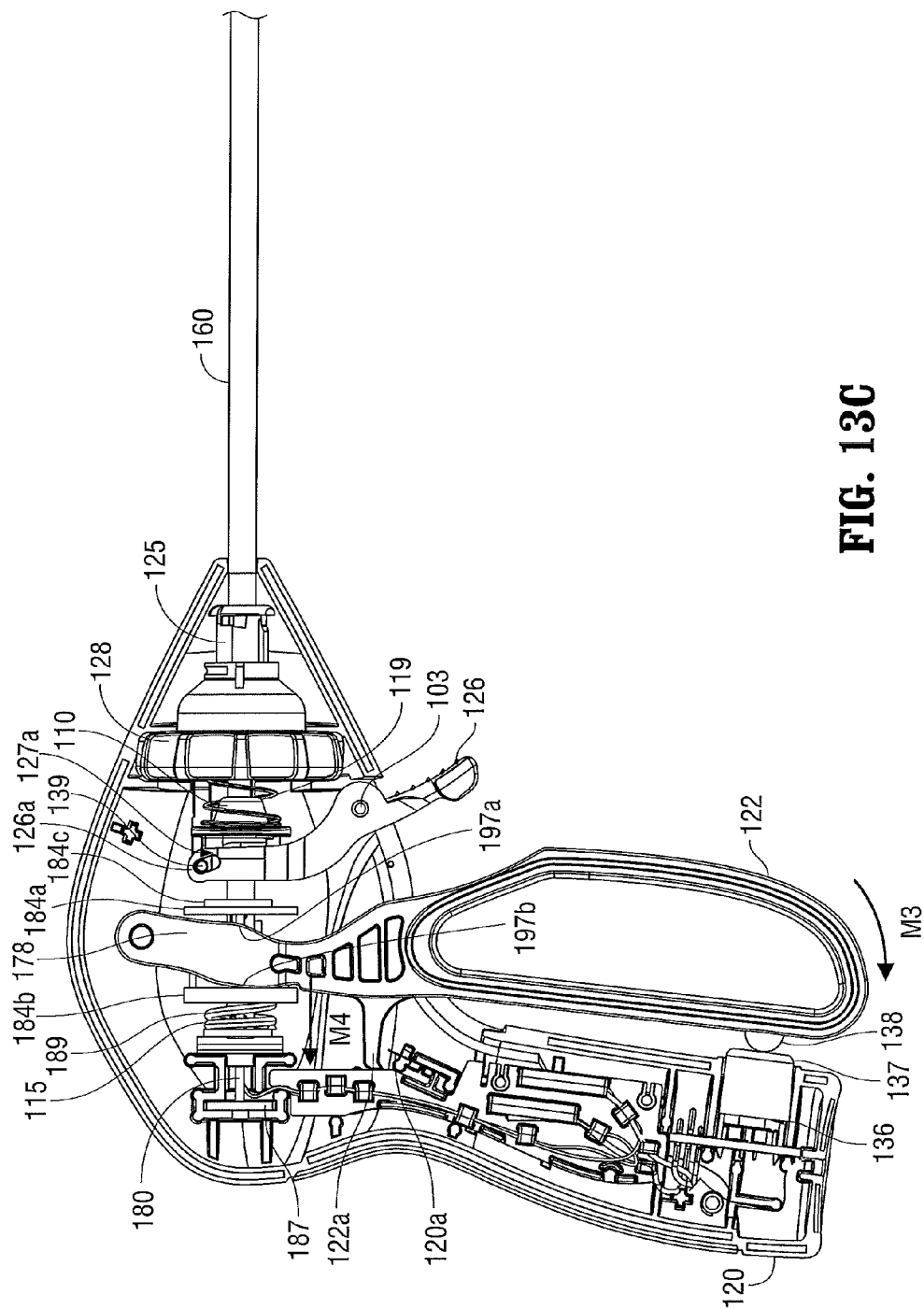
FIG. 13C is a side view of the proximal portion of the instrument of FIG. 10 depicting the movable handle in an approximated configuration with respect to the stationary handle, which corresponds to a second closed configuration of the end effector wherein the jaw members apply an appropriate pressure to generate a tissue seal.

Referring now to FIGS. 13A, 13B, 13C and 13D, a sequence of motions may be initiated by moving the movable handle 122 to induce motion of the outer shaft member 160 in order to close the jaws 130, 132, and by moving the trigger 126 to induce motion of the knife collar 110 in order to translate the blade 156 through the knife channel 158. Initially, both the moveable handle 122 and the knife trigger 126 are in a distal or un-actuated position as depicted in FIG. 13A. This arrangement of the moveable handle 122 and trigger 126 sustains the end effector 114 in the open configuration (FIG. 2A) wherein the jaw members 130, 132 are substantially spaced from one another, and the knife blade 156 is in a retracted or proximal position with respect to the jaw members 130, 132. When both the moveable handle 122 and the knife trigger 126 are in the distal, un-actuated position, pivotal motion of the knife trigger 126 in a proximal direction, i.e., toward the stationary handle 120, is passively prohibited by interference between the trigger 126 and moveable handle 122. This interference prohibits advancement of the knife blade 156 through the knife channel 158 when the end effector 114 is in the open configuration. Movable handle 122 may additionally include a protrusion (not shown) or other feature extending distally therefrom that is configured to contact the trigger 126 upon return of the movable handle 122 distally towards the un-actuated position, thereby returning the trigger 126 towards its un-actuated position if not previously returned via the spring 119 (FIG. 11).

The movable handle 122 may be moved from the distal position of FIG. 13A to the intermediate position depicted in FIG. 13B to move the jaw members 130, 132 to the closed configuration (FIG. 2B). As the movable handle 122 pivots in the direction of arrow M1 (FIG. 13B), the drive surface 197b of the movable handle 122 engages the proximal rim 184b of the drive collar 184. The drive collar 184 is driven proximally such that the spring 189 biases the proximal spring stop 115 and, thus, the outer shaft member 160 is driven proximally in the direction of arrow M2 (FIG. 13B). As discussed above with reference to FIG. 6, proximal movement of the outer shaft member 160 serves to translate the cam pin 192 distally though the cam slots 130c, 132c (FIG. 3A) of the jaw members 130, 132, respectively, and thus pivot jaw member 130 toward jaw member 132 (FIG. 2B). As the jaw members 130, 132 engage one another and no further pivotal movement of the jaw members 130, 132 may be achieved, further distal movement of the cam pin 192 and further proximal movement of the outer shaft member 160 are prevented.

As the movable handle 122 is moved from the distal position of FIG. 13A to the intermediate position depicted in FIG. 13B, a tooth 122a extending proximally from an upper portion of the moveable handle 122 engages a clicker tab 120a supported within the stationary handle 120 to generate a tactile and/or an audible response. The clicker tab 120a may be constructed of a plastic film, sheet metal, or any suitable material configured to generate a "clicking" sound as the clicker tab 120a is engaged and disengaged by the tooth 122a. This response generated by the clicker tab 120a corresponds to a complete grasping of tissue between the jaw members 130, 132 and serves to indicate to the surgeon that further pivotal motion of the moveable handle 122 in a proximal direction, i.e., toward the stationary handle 120, will cause the button activation post 138 to engage the depressible button 137. As the moveable handle 122 is moved from the intermediate position of FIG. 13B to the actuated or proximal position of FIG. 13C, the button activation post 138 depresses the depressible button 137, thereby activating the switch 136 disposed within the stationary handle 120 to initiate the delivery of electrosurgical energy to the end effector 114 to generate a tissue seal.

Figure 10A:
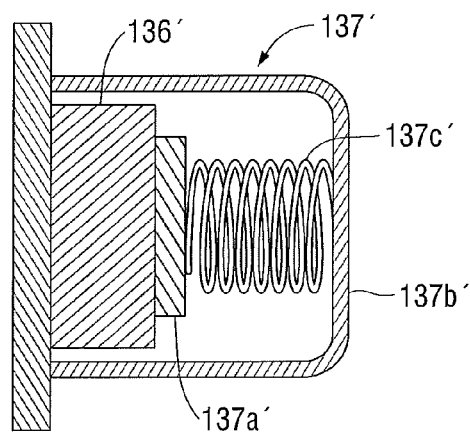
FIG. 10A is a cross-sectional view of another switch and activation button configured for use with the instrument of FIG. 1.

With reference to FIG. 10A, in some embodiments, the depressible button 137' includes an inner button member 137a' operably coupled to the switch 136', an outer button member 137b' disposed about the inner button member 137a', and a spring 137c' disposed between the inner and outer button members 137a', 137b', respectively. In order to activate the switch 136' in such a configuration, the moveable handle 122 (FIG. 10) is moved to the actuated position such that the button activation post 138 (FIG. 10) depresses the outer button member 137b' which, in turn, compresses and urges the spring 137c into contact with the inner button member 137a' to depress the inner button member 137a' and activate the switch 136'. This configuration is advantageous at least in that the biasing force of spring 137c' maintains the switch 136' in an activated state even if handle 122 (FIG. 10) is returned slightly, e.g., moved distally a slight distance. Thus, accidental release of some of the pressure on handle 122 (FIG. 10) will not deactivate the switch 136'.

Referring again to FIGS. 13A, 13B, 13C and 13D, as the movable handle 122 is moved from the intermediate position of FIG. 13B to the actuated or proximal position of FIG. 13C, the pressure applied by the jaw members 130, 132 is increased. As the movable handle 122 pivots further in the direction of arrow M3 (FIG. 13C), the drive surface 197b presses the proximal rim 184b of the drive collar 184 further proximally against the spring 189 in the direction of arrow M4 (FIG. 13C). The spring 189 is compressed against the proximal spring stop 115, and a tensile force is transmitted through the outer shaft member 160 to the jaw members 130, 132. The tensile force supplied by the spring 189 ensures that the jaw members 130, 132 apply an appropriate pressure to effect a tissue seal.

Figure 13D:
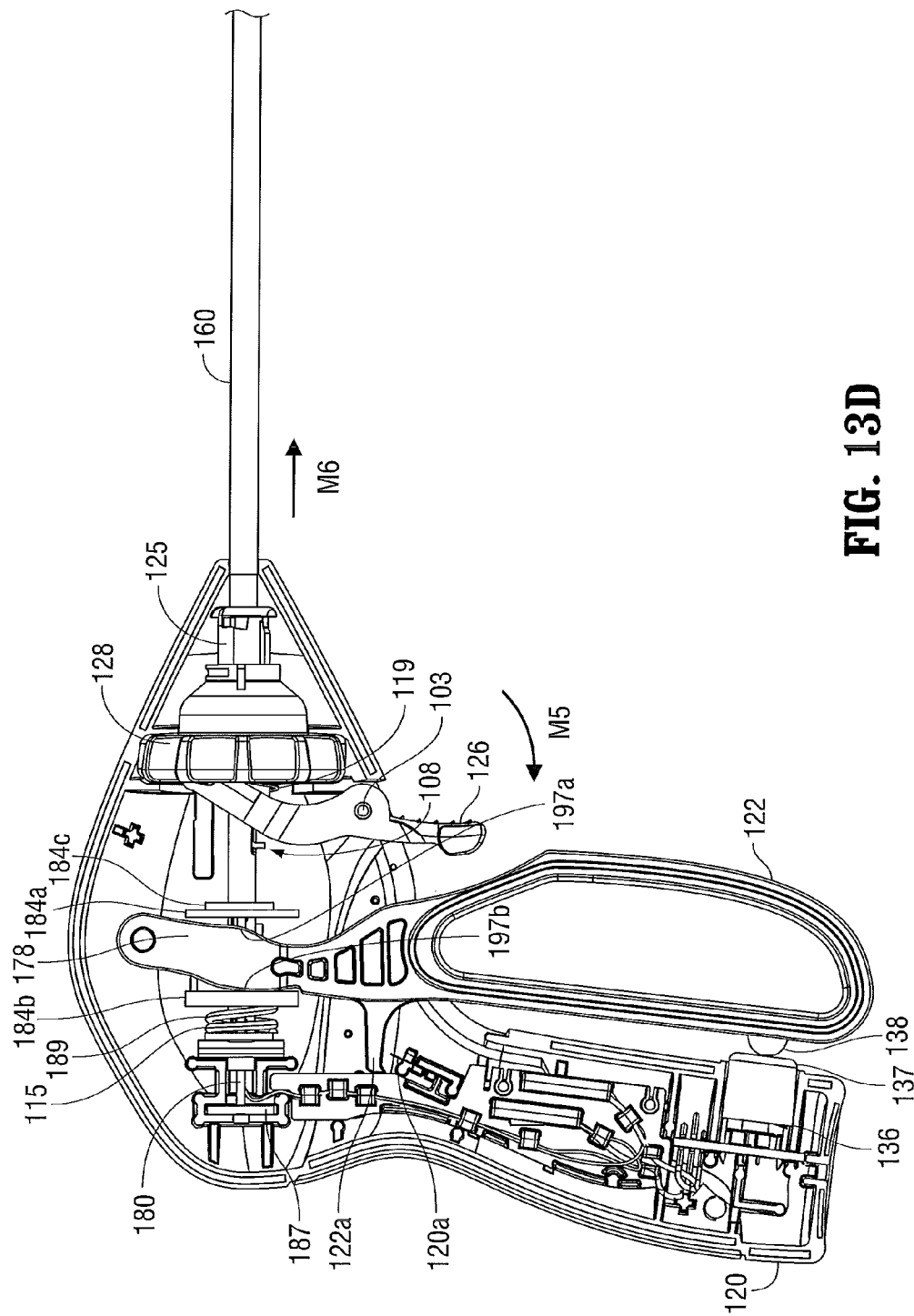
FIG. 13D is a side view of the proximal portion of the instrument of FIG. 10 depicting the knife trigger in an actuated configuration, which corresponds to an actuated or distal position of the knife with respect to the jaw members.

When the movable handle 122 is in the actuated or proximal position, the knife trigger 126 may be selectively moved from the distal position of FIG. 13C to the proximal position of FIG. 13D to advance the knife blade 156 distally through knife channel 158. The knife trigger 126 may be pivoted in the direction of arrow M5 (FIG. 13D), about pivot boss 103 to advance the flanges 126a, 126b of the knife trigger 126 distally in the direction of arrow M6 such that the pin bosses 139a, 139b translate within respective slots 127a, 127b from the position shown in FIGS. 13A-13C to the position shown in FIG. 13D (flange 126b, pin boss 139b, and slot 127b are obstructed from view in FIGS. 13A-13D). Movement of flanges 126a, 126b draws the knife collar 110 distally, which induces distal longitudinal motion of the knife rod 102 by virtue of the coupling of the knife rod 102 to the knife collar 110, as described above with reference to FIG. 12B.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing including an elongated shaft having distal and proximal portions, the proximal portion coupled to the housing, the elongated shaft defining a longitudinal axis;
   a stationary actuation member axially disposed within the elongated shaft, the stationary actuation member including a cam pin mechanically coupled to a distal end thereof;
   an actuating mechanism operably coupled to the proximal portion of the elongated shaft and moveable relative to the housing to selectively cause movement of the elongated shaft along the longitudinal axis relative to the stationary actuation member;
   an end effector including a pair of opposing first and second jaw members operably coupled about a common pivot such that at least one of the jaw members is movable relative to the other jaw member from a first position wherein the jaw members are disposed in spaced relation relative to one another to a second position wherein the jaw members cooperate to grasp tissue therebetween, at least one of the first or second jaw members including a camming slot configured to engage the cam pin to move the at least one movable jaw member between the first position and the second position upon movement of the elongated shaft along the longitudinal axis;
   each jaw member including an electrically conductive tissue sealing surface extending along a length thereof, each tissue sealing surface adapted to connect to a source of electrosurgical energy for conducting electrosurgical energy through tissue grasped therebetween to effect a tissue seal;
   a knife blade supported in the elongated shaft and moveable in a longitudinal direction through a knife channel defined along a length of at least one of the jaw members to cut tissue disposed between the jaw members; and
   a switch supported by the housing and configured to be engaged by the actuating mechanism to initiate delivery of electrosurgical energy from the electrosurgical energy source to the end effector to treat tissue.

2. The surgical instrument according to claim 1, wherein the switch is operably coupled to a depressible button extending from the housing and configured to be selectively engaged by the actuating mechanism.

3. The surgical instrument according to claim 1, wherein the second jaw member is mechanically coupled to a distal end of the elongated shaft and the first jaw member is configured to move relative to the second jaw member.

4. The surgical instrument according to claim 1, wherein the stationary actuation member includes a longitudinal recess formed along a length thereof, the longitudinal recess configured to permit movement of the pivot pin in a longitudinal direction upon movement of the elongated shaft.

5. The surgical instrument according to claim 1, wherein the actuation mechanism is configured to engage a mechanical interface disposed within the housing, the mechanical interface configured to generate a response to engagement with the actuation mechanism upon movement thereof relative to the housing.

6. The surgical instrument according to claim 5, wherein the mechanical interface is constructed of a plastic film.

7. The surgical instrument according to claim 5, wherein the mechanical interface is constructed of sheet metal.

8. The surgical instrument according to claim 5, wherein the response corresponds to the second position of the at least one jaw member.

9. The surgical instrument according to claim 5, wherein the response indicates a position of the actuation mechanism relative to the switch.

10. The surgical instrument according to claim 5, wherein the response is at least one of tactile and audible.

11. The surgical instrument according to claim 1, wherein the actuation mechanism includes a handle moveable relative to the housing between a distal position to move the at least one jaw member to the first position and a proximal position to move the at least one jaw member to the second position.

12. The surgical instrument according to claim 11, wherein the handle engages the switch upon movement thereof to the proximal position.

13. The surgical instrument according to claim 11, wherein movement of the knife blade in a longitudinal direction is prevented when the handle is in the distal position.

14. The surgical instrument according to claim 1, wherein at least one of the jaw members includes an insulator coupled thereto, the insulator configured to electrically insulate the electrically conductive tissue sealing surface from the jaw member.

15. The surgical instrument according to claim 14, wherein the insulator forms at least one knife blade guide configured to guide the knife into the knife channel.

16. The surgical instrument according to claim 14, wherein the insulator is configured to control splay of at least one of the jaw members.

17. The surgical instrument according to claim 1, wherein movement of the elongated shaft along the longitudinal axis causes corresponding movement of at least one of the first or second jaw members along the longitudinal axis to move the at least one camming slot relative to the cam pin.

18. The surgical instrument according to claim 1, wherein the end effector is coupled to the distal portion of the elongated shaft and movement of the elongated shaft along the longitudinal axis moves at least one of the first or second jaw members along the longitudinal axis to move the at least one movable jaw member between the first and second positions.

19. A surgical instrument, comprising:
   a housing;
   an elongated shaft including distal and proximal portions, the proximal portion coupled to the housing, the elongated shaft defining a longitudinal axis;
   an actuating mechanism operably coupled to the proximal portion of the elongated shaft and moveable relative to the housing to selectively cause movement of the elongated shaft along the longitudinal axis;
   an end effector supported by the distal portion of the elongated shaft, the end effector adapted for treating tissue and including first and second jaw members pivotally coupled to one another to move between open and closed configurations, wherein each of the jaw members includes a camming surface thereon;

a switch supported by the housing and configured to be engaged by the actuating mechanism to initiate treatment of tissue;

a knife rod extending at least partially through the elongated shaft and selectively movable in a longitudinal direction, a blade operably coupled to the knife rod extendable through a knife channel defined along a length of at least one of the jaw members; and an inner actuation member extending at least partially through the elongated shaft, the elongated shaft selectively movable in a longitudinal direction with respect to the knife and with respect to the inner actuation member, the inner actuation member carrying a cam pin positioned to engage the camming surface of each of the jaw members to induce the jaw members to move between the open and closed configurations.

20. An electrosurgical system for performing electrosurgery, comprising:

an electrosurgical generator configured to provide electrosurgical energy;

an electrosurgical instrument, comprising:

a housing including an elongated shaft having distal and proximal portions, the proximal portion coupled to the housing, the elongated shaft defining a longitudinal axis;

a stationary actuation member axially disposed within the elongated shaft, the stationary actuation member including a cam pin mechanically coupled to a distal end thereof;

an actuating mechanism operably coupled to the proximal portion of the elongated shaft and moveable relative to the housing to selectively cause movement of the elongated shaft along the longitudinal axis relative to the stationary actuation member;

an end effector including a pair of opposing first and second jaw members operably coupled about a common pivot such that at least one of the jaw members is movable relative to the other jaw member from a first position wherein the jaw members are disposed in spaced relation relative to one another to a second position wherein the jaw members cooperate to grasp tissue therebetween, at least one of the first or second jaw members including a camming slot configured to engage the cam pin to move the at least one movable jaw member between the first position and the second position upon movement of the elongated shaft along the longitudinal axis;

each jaw member including an electrically conductive tissue sealing surface extending along a length thereof, each tissue sealing surface configured to connect to the electrosurgical generator for conducting electrosurgical energy through tissue grasped therebetween to effect a tissue seal;

a knife blade supported in the elongated shaft and moveable in a longitudinal direction through a knife channel defined along a length of at least one of the jaw members to cut tissue disposed between the jaw members; and a switch supported by the housing and configured to be engaged by the actuating mechanism to initiate delivery of electrosurgical energy from the electrosurgical generator to the end effector to treat tissue.

* * * * *